United States Patent
Huang

(10) Patent No.: US 11,026,895 B2
(45) Date of Patent: Jun. 8, 2021

(54) MEDICATED PLASTER FOR TREATING WAIST PAIN

(71) Applicant: SHANGHAI JUKU COSMETIC CO., LTD., Shanghai (CN)

(72) Inventor: Xun Huang, Shanghai (CN)

(73) Assignee: SHANGHAI JUKU COSMETIC CO., LTD., Shanghai (CN)

( * ) Notice: Subject to any disclaimer, the term of this patent is extended or adjusted under 35 U.S.C. 154(b) by 97 days.

(21) Appl. No.: 16/254,972

(22) Filed: Jan. 23, 2019

(65) Prior Publication Data
US 2020/0230072 A1 Jul. 23, 2020

(51) Int. Cl.
| | | |
|---|---|---|
| *A61K 36/00* | (2006.01) | |
| *A61K 9/70* | (2006.01) | |
| *A61K 35/618* | (2015.01) | |
| *A61K 36/28* | (2006.01) | |
| *A61P 29/00* | (2006.01) | |
| *A61K 36/355* | (2006.01) | |
| *A61K 36/534* | (2006.01) | |
| *A61K 36/185* | (2006.01) | |

(52) U.S. Cl.
CPC .......... *A61K 9/7007* (2013.01); *A61K 35/618* (2013.01); *A61K 36/185* (2013.01); *A61K 36/28* (2013.01); *A61K 36/355* (2013.01); *A61K 36/534* (2013.01); *A61P 29/00* (2018.01)

(58) Field of Classification Search
None
See application file for complete search history.

Primary Examiner — Qiuwen Mi
(74) Attorney, Agent, or Firm — Nixon & Vanderhye, PC

(57) ABSTRACT

The present invention discloses a medicated plaster for treating waist pain, comprising, by weight parts, the following raw materials: Abalone shell 10-20; Fructus *Xanthii* 10-20; Herba Lysimachiae 15-20; *Lonicera japonica* 10-15; and mint oil 2-4.

4 Claims, No Drawings

MEDICATED PLASTER FOR TREATING WAIST PAIN

TECHNICAL FIELD

The present invention relates to the field of Chinese medicine, and especially relates to a medicated plaster for treating waist pain.

BACKGROUND

Many people often suffer from waist pain caused by various factors, such as traumatic injury, excessive sexual intercourse, kidney-yang deficiency and kidney-yin deficiency, lumbar muscle degeneration, prolapse of lumbar intervertebral disc, etc. As to waist pain without obvious trauma and internal injuries (bleeding and fracture), there is no effective treatment method. At present, massage therapy is one of the main treatment methods.

A medicated plaster for treating waist pain-applying therapy, in which the medicated plaster for treating waist pain acts through the skin, is one of the commonly used external treatment methods in traditional Chinese medicine clinical applications; the medicated plaster for treating waist pain-applying therapy follows the principles of syndrome differentiation and treatment in Chinese medicine as well as the efficacy, the indications and the channel tropism of the Chinese medicine; and thus the medicated plaster for treating waist pain-applying can sufficiently exert the synergistic effect of all of the Chinese medicine raw materials to provide a multi-medicine compound prescription, so as to achieve a good medicinal effect. Since the medicated plaster for treating waist pain is directly applied on a body surface at the position of waist, most of the medicinal raw materials used to make the medicated plaster for treating waist pain are thick in smell and a channel-ushering medicine with fragrant incense and high migration is further employed, and they permeate into the skin and enter into the meridians and the viscera, so as to achieve the effects of regulating Qi and blood, dredging meridians, dispelling cold-dampness, relieving swelling and pain, etc.

The Chinese medicine surgical medicated plaster for treating waist pain follows Chinese medicine channel tropism principle, utilizes the synergistic effect of the Chinese medicine raw materials, and provides a multi-medicine compound prescription, so as to achieve a good medicinal effect. Since the medicated plaster for treating waist pain is directly applied to the fleshy exterior, the medicated plaster for treating waist pain employs medicinal raw materials which are thick in smell, and further comprises a guide-medicine which can guide the medicine group, so as to remove stagnation and directly act on the nidus. Therefore, the medicated plaster for treating waist pain can permeate into the skin and achieve the effects of diminishing inflammation, relieving pain, activating blood circulation to dissipate stasis, dredging meridians, inducing resuscitation and penetrating bone, dispelling cold-dampness, etc. The medicated plaster for treating waist pain applied to the body surface stimulates the nerve endings and causes nervous reflex, in turn to dilate the blood vessels, promote local blood circulation and improve the nutrition of the surrounding tissues, so as to achieve the purpose of diminishing swelling and inflammation and relieving pain. At the same time, the medicines penetrate into the subcutaneous tissues at the affected part through the skin, and generates the relative advantage of local medicine concentration, to thereby exert a strong pharmacological effect. In addition, the medicated plaster for treating waist pain contains some intensely irritant medicines which can generate strong stimulation, and such strong stimulation can cause nervous reflex, in turn to regulate the body function, promote antibody formation and improve human immunity. After the medicines penetrate the skin and mucous membranes, they enter into the systemic circulation through blood vessels or lymphatic vessels, to exert a systemic medicinal effect.

SUMMARY OF THE INVENTION

The objective of the present invention is to overcome the health-care efficacy shortage of the medicated plasters for treating waist pain in the prior art, and to provide a medicated plaster for treating waist pain which can alleviate waist pain caused by traumatic injury, excessive sexual intercourse, kidney-yang deficiency and kidney-yin deficiency, lumbar muscle degeneration, etc.

For this purpose, the present invention provides a medicated plaster for treating waist pain, comprising, by weight parts, the following raw materials: Abalone shell 10-20; Fructus *Xanthii* 10-20; Herba Lysimachiae 15-20; *Lonicera japonica* 10-15; and mint oil 2-4; and the medicated plaster for treating waist pain is prepared by the following steps:

mixing all of above raw materials to obtain a mixture, and grinding the mixture by adding water to obtain a paste;

decocting the paste with water under gentle fire for 30-60 min, wherein the water is in an appropriate amount for keeping the state of the paste;

cooling above heated paste to obtain a cooled paste medicine;

and applying the cooled paste medicine on a waist pain-treating medicated plaster cloth.

For use, the above medicated plaster for treating waist pain only needs to be applied at a required position, to effectively alleviate various pains at the position of waist.

The medicated plaster for treating waist pain provided by the present invention has the advantages of quick effect, no dependency, no need of oral administration, etc.

Other features and advantages of the present invention will be illustrated in detail in the following specific embodiments.

DETAILED DESCRIPTION OF THE EMBODIMENTS

Generally, the present invention provides a medicated plaster for treating waist pain, comprising, by weight parts, the following raw materials: Abalone shell 10-20; Fructus *Xanthii* 10-20; Herba Lysimachiae 15-20; *Lonicera japonica* 10-15; and mint oil 2-4; and the medicated plaster for treating waist pain is prepared by the following steps:

mixing all of above raw materials to obtain a mixture, and grinding the mixture by adding water to obtain a paste;

decocting the paste with water under gentle fire for 30-60 min, wherein the water is in an appropriate amount for keeping the state of the paste;

cooling above heated paste to obtain a cooled paste medicine;

and applying the cooled paste medicine on a waist pain-treating medicated plaster cloth.

For use, the above medicated plaster for treating waist pain only needs to be applied at a required position of the waist, to effectively alleviate pain at this position.

Hereafter, the present invention will be described in detail with reference to the examples.

Examples 1-5

The examples 1-5 are used to illustrate the medicated plaster for treating waist pain provided by the present invention.

In the examples 1-5, the medicated plasters for treating waist pain 1-5 are prepared according to the raw material ratios in Table 1.

TABLE 1

| Example | Abalone shell (g) | Fructus Xanthii (g) | Herba Lysimachiae (g) | Lonicera japonica (g) | Mint oil(g) |
|---|---|---|---|---|---|
| Example1 | 100 | 100 | 160 | 120 | 20 |
| Example2 | 150 | 150 | 160 | 120 | 20 |
| Example3 | 180 | 150 | 170 | 120 | 30 |
| Example4 | 180 | 160 | 170 | 130 | 40 |
| Example5 | 200 | 200 | 180 | 140 | 40 |

Experimental Examples 1-3

The experimental examples 1-3 are used for illustrating the pain alleviation effects of the medicated plasters for treating waist pain provided by the present invention.

(1) Alleviation for Waist Pain Caused by Excessive Continuous Sexual Intercourse 150 male or female experimenters (aged 25-40 years) who have experienced sexual intercourse or masturbation for more than 4 times within 1 week or have experienced sexual intercourse or masturbation for more than 15 times within 1 month were selected and randomly divided into five groups (with 30 experimenters in each group) corresponding to the examples 1-5. The medicated plasters for treating waist pain provided by the present invention were applied by the 5 groups, respectively. After 1 week, the effects were observed. Compared with a condition before application, the experimenter whose pain symptom completely disappeared was marked as ○, the experimenter whose pain symptom was remarkably alleviated was marked as Δ, and the experimenter whose pain symptom had no remarkable alleviation was marked as x. The effects were shown in Table 2.

TABLE 2

| | Effects (number of experimenters) | | |
|---|---|---|---|
| Group | ○ | Δ | x |
| 1 | 19 | 6 | 5 |
| 2 | 22 | 4 | 4 |
| 3 | 23 | 4 | 3 |
| 4 | 28 | 1 | 1 |
| 5 | 26 | 3 | 1 |

It can be seen from above experimental results that, the medicated plasters for treating waist pain provided by the present invention can effectively alleviate the waist pain caused by excessive sexual intercourse.

(2) Alleviation for Waist Pain Caused by Traumatic Injury without Obvious Trauma Among the patients who have suffered from sprain at the positions of waist and the like or other traumatic injuries, 150 male or female patients (aged 20-35 years) with sprain symptoms at different degrees were selected and randomly divided into five groups (with 30 patients in each group) corresponding to the examples 1-5. The medicated plasters for treating waist pain provided by the present invention were applied by the 5 groups, respectively. After 1 week, the effects were observed. Compared with a condition before application, the patient whose pain symptom completely disappeared was marked as ○, the patient whose pain symptom was remarkably alleviated was marked as Δ, and the patient whose pain symptom had no remarkable alleviation was marked as x. The effects were shown in Table 3.

TABLE 3

| | Effects (number of patients) | | |
|---|---|---|---|
| Group | ○ | Δ | x |
| 1 | 17 | 10 | 3 |
| 2 | 18 | 8 | 4 |
| 3 | 21 | 6 | 3 |
| 4 | 20 | 8 | 2 |
| 5 | 17 | 8 | 5 |

It can be seen from above experimental results that, the medicated plasters for treating waist pain provided by the present invention can sufficiently exert the synergistic effect of all of the Chinese medicine raw materials, and can directly act on the injury positions, so as to effectively alleviate the waist pain caused by various injuries.

(3) Alleviation for Waist Pain Caused by Lumbar Muscle Degeneration 150 male or female testers (aged 20-40 years) who have suffered from waist pain caused by chronic lumbar muscle degeneration were selected and randomly divided into five groups (with 30 testers in each group) corresponding to the examples 1-5. The medicated plasters for treating waist pain provided by the present invention were applied by the 5 groups, respectively. After 1 week, the effects were observed. Compared with a condition before application, the tester whose pain symptom completely disappeared was marked as ○, the tester whose pain symptom was remarkably alleviated was marked as Δ, and the tester whose pain symptom had no remarkable alleviation was marked as x. The effects were shown in Table 4.

TABLE 4

| | Effects (number of testers) | | |
|---|---|---|---|
| Group | ○ | Δ | x |
| 1 | 16 | 9 | 5 |
| 2 | 18 | 8 | 4 |
| 3 | 22 | 4 | 4 |
| 4 | 20 | 4 | 5 |
| 5 | 19 | 7 | 3 |

It can be seen from above experimental results that, the medicated plasters for treating waist pain provided by the present invention has a powerful treatment and alleviation effect for the treatment of the waist pain caused by lumbar muscle degeneration, can sufficiently exert the medicine property of each Chinese medicine raw material and the synergistic effect thereof, and can remarkably alleviate the tester's pain only by external use; and the medicated plasters for treating waist pain provided by the present invention have no obvious toxic and side effects.

For use, the above medicated plaster for treating waist pain only needs to be applied at a required position, to effectively alleviate waist pain at this position caused by various factors.

The invention claimed is:

1. A method of treating waist pain comprising applying to a patient in need thereof a therapeutically effective amount of a medicated plaster comprising, by weight parts, the following raw materials: Abalone shell 10-20; Fructus *Xanthii* 10-20; Herba Lysimachiae 15-20; *Lonicera japonica* 10-15; and mint oil 2-4.

2. The method according to claim 1, wherein the medicated plaster comprises, by weight parts, the following raw materials: Abalone shell 15; Fructus *Xanthii* 15; Herba Lysimachiae 16; *Lonicera japonica* 12; and mint oil 2.

3. The method according to claim 1, wherein the medicated plaster comprises, by weight parts, the following raw materials: Abalone shell 18; Fructus *Xanthii* 15; Herba Lysimachiae 17; *Lonicera japonica* 12; and mint oil 3.

4. The method according to claim 1, wherein the medicated plaster comprises, by weight parts, Abalone shell 18; Fructus *Xanthii* 16; Herba Lysimachiae 17; *Lonicera japonica* 13; and mint oil 4.

\* \* \* \* \*